United States Patent [19]
Kunz et al.

[11] Patent Number: 5,502,180
[45] Date of Patent: Mar. 26, 1996

[54] INULIN DERIVATIVES, PROCESS FOR THEIR PREPARATION AND THEIR USE

[75] Inventors: Markwart Kunz, Worms; Alireza H. Begli, Ramsen, both of Germany

[73] Assignee: Südzucker AG Mannheim/Ochsenfurt, Germany

[21] Appl. No.: 288,072

[22] Filed: Aug. 10, 1994

[30] Foreign Application Priority Data

Aug. 10, 1993 [DE] Germany ............ 43 26 782.3

[51] Int. Cl.$^6$ ............ A61K 31/715; C08B 37/18; C07H 1/00; C07G 17/00
[52] U.S. Cl. ............ 536/123; 536/124; 536/128
[58] Field of Search ............ 514/54; 536/123, 536/128, 124

[56] References Cited

U.S. PATENT DOCUMENTS

| | | | |
|---|---|---|---|
| 3,336,291 | 8/1967 | Patton et al. | 260/231 |
| 4,143,666 | 3/1979 | Rainer et al. | 131/2 |
| 4,421,852 | 12/1983 | Hoehn et al. | 435/99 |
| 4,585,858 | 4/1986 | Moltsky | 536/4.1 |
| 4,609,640 | 9/1986 | Morishita et al. | 514/12 |
| 4,613,377 | 9/1986 | Yamazaki et al. | 127/39 |
| 4,661,294 | 4/1987 | Holick et al. | 514/167 |
| 4,871,574 | 10/1989 | Yamazaki et al. | 426/622 |
| 4,954,622 | 9/1990 | Cooper | 536/127 |
| 4,968,785 | 11/1990 | Moser et al. | 536/124 |
| 5,051,408 | 9/1991 | Cooper | 514/54 |
| 5,169,671 | 12/1992 | Harada et al. | 426/658 |
| 5,346,929 | 9/1994 | Guttag | 523/124 |

FOREIGN PATENT DOCUMENTS 0539235 4/1993 European Pat. Off. .

OTHER PUBLICATIONS

Chemical Abstracts, vol. 102, 1985, p. 664.

Primary Examiner—Ronald W. Griffin
Attorney, Agent, or Firm—Finnegan, Henderson, Farabow, Garrett, Dunner

[57] ABSTRACT

The present invention relates to inulin derivatives of the general formula I

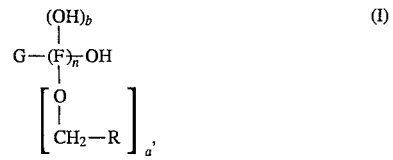

in which R=—CH$_2$OH, —CHOH—(CH$_2$)$_m$—CH$_3$, m is an integer from 0 to 10, n is on average a number from 10 to 50, a and b is a number from 0 to 3, where a+b=3, G is a glucopyranose group and F is a fructofuranose group, to a process for their preparation and to their use.

6 Claims, No Drawings

INULIN DERIVATIVES, PROCESS FOR THEIR PREPARATION AND THEIR USE

The present invention relates to novel inulin derivatives, a process for their preparation and their use.

Naturally occurring polysaccharides are used, by reason of their functional properties, in a variety of industrial sectors such as, for example, the textiles, paper, building, ceramics and plastics industries. This use is in most cases preceded by derivatization appropriate for the application. The particular advantage of such compounds is that they are produced from "renewable raw materials" and undergo substantial biodegradation.

The preconditions for wide use are, besides easy availability and a favorable price, a constant quality and the possibility of specific and reproducible derivatization.

Although the polysaccharides used customarily to date, namely cellulose and starch, are available in any desired quantity and in a high and constant quality at a favorable price, they exhibit considerable problems in derivatization.

It is true that cellulose is a polymer with a linear and homogeneous structure composed of β-1-4-glucosidically linked anhydroglucose units; however, its crystallinity makes it extremely resistant to derivatization. Thus, cellulose derivatives can be obtained only under difficult reaction conditions, in some cases using environmentally hazardous chemicals. The high degree of polymerization of cellulose and the low solubility of the derivatives associated therewith also limit the utilizability. Degradation of the cellulose by enzymes or acids leads to very inhomogeneous fragments, which again makes derivatization difficult.

Although starch is easier to derivatize it consists, by contrast, of a heterogeneous system. Besides the amylose which has a linear structure and an α-1-4-glucosidic linkage, it contains a component which is called amylopectin and is branched by 1-6-glucosidic linkages and whose content in the starch may additionally range up to 80%. Since amylose and amylopectin differ greatly from one another in structue and properties, and they occur in very variable proportions in the various starches, specific derivatization of the starch is impossible.

Inulin is a polysaccharide belonging to the fructan group and occurs in economically obtainable amounts in parts of various plants such as, for example, Jerusalem artichoke and dahlia tubers and in chicory roots. Inulin consists of β-2-1-linked chains which have a linear structure and comprise, in general, up to 50 β-O-fructofuranose molecules which are terminated at the reducing end in each case by an α-D-glucopyranose unit. The average chain length and molecular weight distribution depend both on the plant species and on the growth phase and the preparation method. Average chain lengths of 10 to 25 are usual, in which case the individual molecules have about 5 to 50 fructose units.

Although inulin has been known for a very long time it has not been used widely as yet. Its industrial use is confined at present to the direct use as foodstuff components such as, for example, as bulking agent or fat substitute for producing low-calorie food and for producing fructose syrups and fructooligosaccharides by means of acidic or enzymatic hydrolysis.

It is furthermore known, from E. Schacht et al. in J. Controlled Release 1984, 1 (1), 33–46, that it is possible, by preceding oxidation, to couple dextran or inulin to pharmaceuticals such as procainamide. At the same time, the article describes the activation of said polysaccharides with epichlorohydrin. However, since epichlorohydrin, which is known to be a bifunctional reagent, causes branching or crosslinking of the polysaccharide framework, depending on the reaction condition (Modified starches: properties and uses: O. B. Würzburg, (1986) pages 43–44), this reaction does not result in homogeneous derivatives.

EP 0 539 235 A2 discloses low-calorie foodstuffs such as fat substitutes which are produced by suspending polysaccharides, in particular starch and cellulose, in hydrocarbons such as toluene or xylene, catalyzing with aqueous alkali metal hydroxide, removing the added water by distillation, and subsequently etherifying the activated polysaccharide under high pressure and at high temperature with alkyl epoxides. The resulting derivatives are subsequently esterified with $C_8$-$C_{24}$ fatty acids. The polysaccharides mentioned herein are primarily starch and cellulose, but may also be polydextrose, xylan, mannan or a not specifically defined inulin. The process used in this case for the alkoxylation is disclosed in U.S. Pat. Nos. 4,585,858 and 3,336,291 in particular for starch and cellulose. In this case too there are considerable problems in the derivatization of the polysaccharides because of the structure.

An object of the invention is, on the one hand, to provide novel epoxidized inulin derivatives of uniform substitution. Epoxidized inulin derivatives as claimed in the main claim and, in preferred form, in dependent claim 2 and 3 are proposed to achieve this object.

On the other hand, an object of the invention is to propose a process for the derivatization of inulin and for the preparation of the abovementioned epoxidized inulin derivatives, and finally their use. A preparation process as claimed in claim 4 and 5, and the use of the epoxidized inulins as claimed in claim 6, are proposed to achieve these objects.

It has emerged, surprisingly, that the derivatization of inulin can be carried out in homogeneous phase, in contrast to starch and cellulose, because of its chemical structure, its solubility in water and the relatively low viscosity in aqueous solutions. This dispenses with the typical problems of carrying out a heterogeneous reaction; uniform distribution of the reagents as well as better steric accessibility are achieved, which leads to a homogeneous distribution of the substituents in the desired final product.

The compounds according to the invention are prepared by etherifying an inulin of the formula II

in which n defines the average chain length and is a number from 10 to 50, preferably >15 and, in particular, >20, G is a glucopyranose group and F is a fructofuranose group, whose three free OH groups are additionally depicted, in a aqueous solution, in the presence of a basic catalyst with epoxides of the general formula III

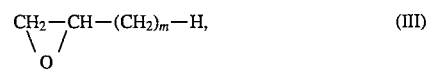

in which m is an integer from 0 to 10, to form inulin derivatives of the general formula:

in which
R=—CH$_2$OH, —CHOH(CH$_2$)$_m$—CH$_3$,
m is an integer from 0 to 10,
n is on average a number from 10 to 50, a and b is a number from 0 to 3, where a+b=3,
G is a glucopyranose group and
F is a fructofuranose group.

The reaction is carried out with concentrations from 20 to 50% by weight at a temperature of 40° to 100° C. In order to be able to prepare a derivative with the desired degree of substitution it suffices to change the stoichiometric ratio of the reactants. The degree of substituion (DS) is indicated as the ratio of the alkyl groups to the fructose units, there being, as a rule, substitution of several fructose units in each inulin molecule. Since each fructose unit has 3 free hydroxyl groups, multiple substitution is also possible. Degrees of substitution from 0.1 to 2 and preferably of 0.5–1 are advantageous for most applications.

The so-called crude inulin obtained from plant parts can be used directly in the process according to the invention, but the final products obtained in this case are inhomogeneous in respect of molecular weight. It is therefore advantageous to use a long-chain inulin, for example having an average chain length>15, in particular >20, fructose units, from which the short-chain constituents with, for example, ≦10 to 12 fructose units have been removed. Products of this type can be prepared by the process described in DE 43 16 425-A1. Alternatively, the lower chains can be removed by chromatography, or the longer chains can be obtained by precipitation from an aqueous solution with alcohol.

Catalysts suitable for the reaction are alkalin metal and alkaline earth metal hydroxides as well as other catalysts known for etherification reactions, and sodium hydroxide and strongly basic, OH-loaded anion exchangers are particularly preferred. The amount of catalyst used varies as a function of the reactivity of the substituents employed and is, in general, 2 to 10% by weight of the inulin initially present.

Since both the reactivity of the substituents and their solubility in water decrease as the alkyl chain length increases, the efficiency of the reaction can be increased by carrying it out in the presence of a small amount of a solubilizer such as isopropanol. The solubility of the products with long alkyl chains can be additionally increased by using, in place of native inulin, inulin derivatives which have already been partially derivatized with short-chain epoxides.

The reaction itself can be carried out in apparatus suitable for the purpose under atmospheric pressure or under elevated pressure, continuously or else batchwise. The reaction is, as a rule, complete after 6 to 24 h.

In the case of etherification with water-miscible epoxides, the reaction can be carried out in a suitable reactor, for example in a tubular reactor using a strongly basic, OH-loaded anionic exchanger in place of alkali metal or alkaline earth metal hydroxides under fixed bed or fluidized bed conditions. In this case, a clear 20 to 40% by weight inulin solution is pumped through a tubular reactor which is maintained at 50° to 70° C. and is packed with anion exchange resin and, at the same time, the reagent is metered in through a separate line with thorough mixing.

This procedure has the advantage that neutralization of the reaction product is dispensed with. However, it is advisable previously to remove salts from the inulin employed.

If the reaction is catalyzed with alkali metal or alkaline earth metal hydroxide, it is advisable subsequently to neutralize the resulting product. This is expediently carried out with dilute hydrochloric acid or with an $H^+$-loaded weakly acidic cation exchanger. After drying, these products are immediately suitable for a large number of applications.

Furthermore, after the neutralization, the derivative can be purified by chromatographic separation on a $Ca^{++}$- or $K^+$- or $Na^+$-loaded, slightly crosslinked, strongly acidic cation exchange resin (for example Duolite (Tm) C204 from Rohm und Haas) and converted by suitable drying methods, for example freeze- or spray-drying, into the dry form.

The inulin derivatives prepared in this way are white, odorless substances which are soluble in cold water and have, depending on the degree of substitution and alkyl chain length of the substituent, interesting properties, particularly in respect of their solubility, surface activity and viscosity.

The alkoxylated derivatives are more soluble in cold water than is the inulin employed. It is possible without difficulty to prepare concentrated solutions of the derivatives, such as, for example, a 50% by weight solution at 25° C.

The inulin derivatives synthesized according to the invention exhibit an inverse solution behavior depending on the temperature and the degree of substitution. At temperatures of 45°–60° C., they flocculate out of their aqueous solutions and redissolve on cooling again. Furthermore, they are soluble in the customary organic solvents such as, for example, MeOH, EtOH, DMF and DMSO, and the solubility in protic as well as in aprotic solvents correlates with the structural parameters such as alkyl chain length and degree of substitution. The number average molecular weight (Mn) of the synthesized inulin derivatives is, according to osmometric determination, in the range from 3000 to 5500 g/mol, and the corresponding viscosities of the 3% by weight solutions of the inulin derivatives at 20° C. are between 15 and 25 mPa.s.

The inulin derivatives prepared according to the invention are therefore suitable as polymeric plasticizers for thermoplastics or for sheets produced using starch and starch derivatives, cellulose or cellulose derivatives, auxiliaries for the building, ceramics and paper industries, emulsifiers and stabilizers, size materials for the textiles industry, carrier materials for pharmaceutical agents, solubilizers for hydrophobic drugs and cosmetics or as gel-forming polymers.

A crude inulin which had an average chain length of 18 to 20 fructose units and had been purified by alcohol precipitation was used in the following examples. The yield is based in each case on the total of the starting materials. The alkylglycol is produced as by-product in each case by hydrolysis.

EXAMPLE 1

20 g of inulin dry matter (0.123 mol) were dissolved in 60 ml of 0.5M NaOH (6% by weight based on inulin DM) with heating, transferred into a stirred autoclave and there mixed with 7.14 g (0.123 mol) of propylene oxide. The reaction was then carried out under a pressure of 3 bar (nitrogen) at 70° C. with the stirrer rotating at $800 \times min^{-1}$. After 10 hours, the autoclave was decompressed and the resulting product solution was first neutralized to pH 6.5–7.0 with HCl. A chromatography column with an $Na^+$-loaded, slightly crosslinked, strongly acidic cation exchange resin (Duolite® C204) was prepared and the neutralized product solution was separated thereon at 60° C. The propoxyinulin-containing fraction was collected and freeze-dried.
Yield: 92%

Degree of substitution (DS): 0.66
Surface tension σ of a 1% strength solution: 62 mN.m$^{-1}$

EXAMPLE 2

650 g of a 30% by weight inulin solution (≡1.2 mol) were mixed with 9.8 g (5% by weight based on inulin DM) of sodium hydroxide and circulated by pumping into a tubular reactor maintained at 55° C. and equipped with an efficient condenser. 67 g (≡1.2 mol) of propylene oxide were continuously metered into the circulating inulin solution over the course of 60 min. The solution was circulated by pump at 55° C. for a further 6 h.

The resulting product solution was neutralized with the aid of an H$^+$-loaded strongly acidic cation exchanger. After filtration and evaporation to a dry matter content of 40%, the solution was separated on a column packed with chromatography resin (Lewatit® TSW 40-Ca$^{++}$) at 60° C. The propoxyinulin-containing fraction was collected and the propoxyinulin was isolated therefrom as a white powder by spray-drying.
Yield: 85.7%
Degree of substitution (DS): 0.71
Surface tension σ of a 0.1% strength solution: 64 mN.m$^{-1}$

EXAMPLE 3

256 g of inulin dry matter (1.58 mol) were dissolved in 592 g of demineralized water by heating and passed into a stirring vessel equipped with efficient condenser and dropping funnel and maintained at 55° C., and initially 500 ml of an OH$^-$-loaded strongly basic anion exchanger (Amberlite® IRA 900) were added. Then 91.82 g (1.58 mol) of propylene oxide were added dropwise to the solution over the course of 4 hours. The reaction mixture was then stirred at 55° C. for a further 12 h.

The anion exchange resin was then removed by filtration, and the filtrate was neutralized with the aid of an H$^+$-loaded strongly acidic cation exchanger and separated by chromatography. The propoxyinulin was obtained as a white powder by spray-drying the propoxyinulin-containing fraction.
Yield: 85%
Degree of substitution (DS): 0.5
Surface tension σ of a 0.5% strength solution: 58 mN.m$^{-1}$

EXAMPLE 4

250 ml of an OH$^-$-loaded strongly basic anion exchanger (Amberlite® IRA 900) were initially introduced into a tubular reactor equipped with a perforated plate and maintained at 55° C. Then 480 g of a 30% by weight inulin solution (144 g dry matter=0.89 mol) were circulated by pumping from the bottom to the top through the reactor. The flow rate was in this case chosen so that the resin bed was converted into a fluidized bed. Then, over the course of 60 minutes, 51.6 g (0.89 mol) of propylene oxide were metered into the circulating inulin. After reaction for a further 6 hours, the product solution was separated from the catalyst, neutralized and subjected to chromatographic separation. The propoxyinulin-containing fraction was spray-dried, and thus the propoxyinulin was isolated in dry form.
Yield: 87.3%
Degree of substitution (DS): 0.36
Surface tension σ of a 0.5% strength solution: 59 mN.m$^{-1}$

EXAMPLE 5

250 ml of an OH$^-$-loaded strongly basic anion exchanger (Amberlite® IRA 900) were initially introduced into a tubular reactor equipped with a perforated plate and maintained at 55° C. Then 480 g of a 30% by weight inulin solution (144 g dry matter=0.89 mol) were pumped through the reactor. The flow rate was chosen in this case so that it was possible to comply with a total contact time of 8 hours. At the same time, a total of 51.6 g (0.89 mol) of propylene oxide were metered, distributed over the total contact time, into the liquid stream upstream of the reactor. The product solution running out of the reactor was neutralized, and the propoxyinulin was isolated therefrom as a white powder by chromatographic separation with subsequent spray-drying of the relevant fraction.
Yield: 87%
DS: 0.38
Surface tension σ of a 0.5% strength solution: 58 mN.m$^{-1}$

EXAMPLE 6

60 g of propoxylated inulin (with DS=1.33) were dissolved in 200 ml of water and, after addition of 3.0 g of NaOH and 68 g of epoxydodecane, reacted in an autoclave under a pressure of 3 bar (N2), at 80° C. and with the stirrer rotating at 900×min$^{-1}$ for 16 h. The reaction mixture was then extracted with n-hexane, and the aqueous phase was neutralized and the dodecyloxyinulin was obtained therefrom by chromatographic separation and spray-drying.
Yield: 70%
Surface tension σ of a 0.1% strength solution: 29 mN.m$^{-1}$

EXAMPLE 7

| Batch: | 6 g inulin DM in the form of a 30% by weight solution |
| --- | --- |
| | 0.3 g NaOH |
| | 4 g epoxybutane |
| Temperature: | 55° C. |
| Reaction time: | 16 h |
| Yield: | 92% |
| DS | 0.6 |

Surface tension σ of a 0.1% strength solution: 49 mN.m$^{-1}$

EXAMPLE 8

| Batch: | 30 g inulin DM in the form of a 30% by weight solution |
| --- | --- |
| | 65 ml Amberlite ® IRA 900 OH$^-$ |
| | 20 g epoxybutane |
| Temperature: | 55° C. |
| Reaction time: | 16 h |
| Yield: | 78% |

Surface tension a of a 0.1% strength solution: 47 mN.m$^{-1}$
DS 0.36

EXAMPLE 9

| Batch: | 30 g inulin DM in the form of a 30% by weight solution |
| --- | --- |
| | 65 ml Amberlite ® IRA 900 OH$^-$ |
| | 23.2 g 1,2-epoxyhexane |
| Temperature: | 60° C. |
| Reaction time: | 16 h |
| Yield: | 73% |

Surface tension a of a 0.1% strength solution: 43 mN.m$^{-1}$

EXAMPLE 10

| Batch: | 30 g inulin DM in the form of a 30% by weight solution |
| --- | --- |
| | 1.5 g NaOH |
| | 23.2 g 1,2-epoxyhexane |
| Temperature: | 55° C. |
| Reaction time: | 16 h |
| Yield: | 78% |
| DS: | |

Surface tension a of a 0.1% strength solution: 41 mN.m$^{-1}$

EXAMPLE 11

In order to show that the consistency of hydraulic binder systems is beneficially affected by using the inulin derivatives prepared according to the invention, a lime mortar of the following composition was prepared:

EXAMPLE

50% beta-calcium sulphate hemihydrate

20% hydrated lime

29% lime sand (0–1 mm)

0.8% light filler 0.02% starch ether 0.02% air entrainer particles 0.04% retarder 0.17% cellulose ether Corresponding mixtures with 0;.01 to 0.1% by weight alkoxyinulin derivatives according to Examples 2 and 7 were prepared and compared with the basic mortar, and it was found that the technical use properties, specifically the processability, the water-retention capacity and the consistency-providing effect of the conventional thickeners are improved.

EXAMPLE 12

A textile size of the following composition was prepared:

51% sizing starch

17% PVA

30% alkoxyinulin derivative

2% sizing wax

In this formulation, in each case the alkoxyinulin derivatives according to Examples 3, 7 and 8 according to the invention were employed. It emerged from this that the consistency of the modified sizes is improved compared with conventional textile sizes built up on a synthetic basis (PVA, acrylate), starch basis or mixtures thereof, and their elasticity, adhesive power, removability by washing, flow characteristics and weave efficiency is improved.

EXAMPLE 13

A mixture of the following composition was used for sizing paper:

50 to 100 g/l starch 1 to 5 g/l sizing agent (acrylate/methacrylate)

10 to 20 g/l alkoxyinulin derivatives

It emerged that it was possible to improve the surface properties such as breaking length, bonding strength, whiteness, surface smoothness, printability of paper by using the inulin derivatives prepared according to the invention according to Example 2, 6, 8 and 10 in conjunction with acrylate/methacrylate products and starch.

In addition, the alkoxylated inulin derivatives show good protective colloid and emulsifier properties in the production of dispersions of synthetic materials, especially in polyvinyl acetate and their copolymerization dispersions.

Because of their good properties (such as, for example, hydrophilic/hydrophobic character, viscosity, molecular weight etc.), the inulin derivatives are adsorbed particularly well onto the surface of latex particles. The protective layer formed in this way prevents the coagulation of the dispersion during the polymerization and stabilizes the finished dispersion when mechanically stressed.

To test the solubilization capacity of alkoxylated inulins for substances which are insoluble or sparingly soluble in water, by way of example two chromophores (anthracene as UV-active substance and the azo dye Sudan red B which is insoluble in water and absorbs in the visible region) were dispersed in aqueous solutions of the inulin derivatives, and the extinction at wavelengths characteristic in each case (anthracene: $\lambda=371$ and $\lambda=320$ nm, Sudan red B: $\lambda=516$ nm) was measured for various concentrations of the inulin derivatives. For comparison, aqueous dispersions of the two chromophores were prepared and measured without addition of the inulin derivatives.

Whereas no extinctions at the characteristic wavelengths were to be found for the comparison solutions (without inulin derivatives), significant extinctions were determined for the solutions of the inulin derivatives. The solubilization capacity increases with increasing concentration of the inulin derivatives, length of the alkoxy group and the degrees of substitution.

These investigations show that alkoxyinulins are suitable to act as carriers or stabilizers for substances which are sparingly soluble or insoluble in water (additives in cosmetics, pharmaceuticals "prodrugs" "drug targeting" "retarded drug release" "biocompatible drug carrier").

We claim:

1. An inulin compound of the formula

in which

G is a glucopyranose group;

F is a fructofuranose group;

R represents a —CH$_2$OH or —CHOH—(CH$_2$)$_m$—CH$_3$ group;

m is an integer from 0 to 10;

n is on average a number from 10 to 50; and a and b are each a number from 0 to 3, where a+b=3.

2. The inulin compound of claim 1, wherein mixtures with various —O(CH$_2$)—R groups are present.

3. The inulin compound of claim 1 or 2, where n is greater than 15.

4. The inulin compound of claim 1 or 2, where n is greater than 20.

5. A process for the preparation of an inulin compound of claim 1, which comprises heating inulin of the formula

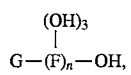 (II)

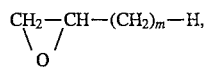

in which G, F and n are the same as defined in claim 1, in an aqueous solution with an alkyl epoxide of the formula $$CH_2\underset{O}{-}CH-(CH_2)_m-H, \quad (III)$$

in which m is an integer from 0 and 10, in the presence of an alkaline catalyst at a temperature from 40° to 100° C. and an inulin concentration of 20 to 50% by weight, and isolating the resulting alkoxyinulin of the formula I.

6. The process of claim 5, wherein an OH-loaded strongly basic anion exchange resin is used as the alkaline catalyst.

* * * * *